United States Patent
Kim et al.

(10) Patent No.: US 9,926,266 B2
(45) Date of Patent: Mar. 27, 2018

(54) PURE ISOPHTHALALDEHYDE BISULFITE ADDUCT AND NOVEL PREPARATION METHOD THEREOF

(71) Applicant: KOREA INSTITUTE OF SCIENCE AND TECHNOLOGY, Seoul (KR)

(72) Inventors: Hyoung-Juhn Kim, Seoul (KR); Eun Ki Kim, Seoul (KR); So Young Lee, Seoul (KR); Jong Hyun Jang, Seoul (KR); Jin Young Kim, Seoul (KR); Sung Jong Yoo, Seoul (KR); Dirk Henkensmeier, Seoul (KR); Dae Ki Choi, Seoul (KR); Jonghee Han, Seoul (KR); Suk Woo Nam, Seoul (KR)

(73) Assignee: KOREA INSTITUTE OF SCIENCE AND TECHNOLOGY, Seoul (KR)

(*) Notice: Subject to any disclaimer, the term of this patent is extended or adjusted under 35 U.S.C. 154(b) by 0 days.

(21) Appl. No.: 15/292,106

(22) Filed: Oct. 12, 2016

(65) Prior Publication Data
US 2018/0050984 A1    Feb. 22, 2018

(30) Foreign Application Priority Data
Aug. 17, 2016    (KR) .................. 10-2016-0104349

(51) Int. Cl.
C07C 303/44    (2006.01)
C07C 303/32    (2006.01)
C07C 309/24    (2006.01)

(52) U.S. Cl.
CPC .......... *C07C 303/44* (2013.01); *C07C 303/32* (2013.01); *C07C 309/24* (2013.01)

(58) Field of Classification Search
None
See application file for complete search history.

(56) References Cited

U.S. PATENT DOCUMENTS 3,620,998 A * 11/1971 Marvel .............. C08G 73/0694
                                                524/173
3,630,972 A * 12/1971 Marvel ................ C07D 235/18
                                                528/149

(Continued)

OTHER PUBLICATIONS

Fishel ("Solution Polymerization of Polybenzimidazole" Journal of Polymer Science, Part A: Polymer Chemistry, 2016, 54, p. 1795-1802) (Year: 2016).*

(Continued)

*Primary Examiner* — Rosalynd A Keys
*Assistant Examiner* — Amy C Bonaparte
(74) *Attorney, Agent, or Firm* — Goldilocks ZONE IP LAW (57) ABSTRACT

Disclosed are a method for preparing a pure isophthalaldehyde bisulfite adduct free from impurities through a specific purification process, and use thereof as a starting material for polymerizing polybenzimidazole under a mild condition. According to the present disclosure, it is possible to obtain a pure isophthalaldehyde bisulfite adduct free from impurities, such as unreacted materials or byproducts. In addition, it is possible to accomplish industrial mass production of a high-molecular weight polybenzimidazole by using the adduct as a starting material for polymerizing polybenzimidazole under a mild condition in an organic solvent.

4 Claims, 5 Drawing Sheets

(56) References Cited

U.S. PATENT DOCUMENTS 3,772,309 A * 11/1973 Marvel ................ C07D 235/18
528/143
2014/0357831 A1* 12/2014 Benicewicz ........... C08G 73/18
528/268

OTHER PUBLICATIONS

Higgins ("Benzimidazole Polymers from Aldehydes and Tetraamines" Journal of Polymer Science: Part A-1, vol. 8, 1970, p. 171-177) (Year: 1970).*
Pense ("Polymers Containing Anthraquinone Units: Polymidazoles and Polypyrrolones from 1,2,5,6-Tetraaminoanthraquinone" Journal of Polymer Science: Part A-1, vol. 8, 1970, p. 3189-2198) (Year: 1970).*
Tai-Shung Chung, A Critical Review of Polybenzimidazoles:Historical Development and Future R&D Journal of Macromolecular Science, Jan. 1997, pp. 277-301, Part C, 37:2.
Herward Vogel et al. Polybenzimidazoles, New Thermally Stable Polymers, Journal of Polymer Science 1961, pp. 511-539 , vol. L.
F. L. Hedberg et al. A New Single-Step Process for Polybenzimidazole Synthesis, Journal of Polymer Science: Polymer Chemistry Edition ,1974, pp. 1823-1828, vol. 12.

* cited by examiner

PURE ISOPHTHALALDEHYDE BISULFITE ADDUCT AND NOVEL PREPARATION METHOD THEREOF

CROSS-REFERENCE TO RELATED APPLICATIONS

This application claims, under 35 U.S.C. § 119, the priority of Korean Patent Application No. 10-2016-0104349 filed on Aug. 17, 2016 in the Korean Intellectual Property Office, the disclosure of which is incorporated herein by reference in its entirety.

TECHNICAL FIELD

The following disclosure relates to a pure isophthalaldehyde bisulfite adduct and a novel method for preparing the same. More particularly, the following disclosure relates to a method for preparing a pure isophthalaldehyde bisulfite adduct free from impurities through a specific purification process and use thereof as a starting material for polymerizing polybenzimidazole under a mild condition.

BACKGROUND

Engineering plastic is a term generally referring to plastic having a lower weight and higher strength, and particular examples thereof include polyimide, polycarbonate, or the like. Polybenzimidazole is a material having the highest thermal strength among such engineering plastics and recently have been used widely as a material for fire-fighting garments, space suits, or the like (Non-patent Document 1).

However, according to the conventional polymerization process for polybenzimidazole, a strongly acidic polyphosphoric acid solvent is used both as a polymerization solvent and as a dehydration reagent, and acidic isophthalic acid is also used as a monomer. Thus, a seriously complicated post-treatment process is required for neutralizing such acidic materials, thereby limiting industrial mass production of polybenzimidazole (Non-patent Document 2).

In addition, a polymerization method for polybenzimidazole using phenylsulfone or sulfolane as a solvent is known. However, the reaction condition has not yet been optimized. Moreover, such a polymerization method is applicable merely at a significantly diluted concentration and thus is not suitable for mass production (Non-patent Document 3).

Meanwhile, many studies and results thereof have been disclosed with reference to polybenzimidazole. However, most of them are limited to introduction of a filler to conventional polybenzimidazole or preparation of a copolymer. Thus, there has been no special study about the polymerization method for polybenzimidazole itself other than the above-mentioned methods.

Under these circumstances, the present inventors have recognized that substitution of such a strongly acidic solvent and monomer used for the conventional polymerization process for polybenzimidazole with another solvent and monomer may facilitate mass production of polybenzimidazole for engineering plastic. Therefore, there has been suggested a novel method for preparing an isophthalaldehyde bisulfite adduct, which is a monomer for use in polymerization of polybenzimidazole under a relatively mild condition in an organic solvent.

Particularly, one of the most important factors in preparing an isophthalaldehyde bisulfite adduct as a monomer is purity. According to the Carothers equation as depicted by the following Formula 1, it can be seen that even a slight decrease in conversion (p, 0≤p≤1) causes a significant decrease in degree of polymerization (DP, $\overline{X}_n$).

[Formula 1]

$$\overline{X}_n = \frac{1}{1-p} \quad \text{(Carothers equation)}$$

Therefore, when the monomer does not have high purity, the conversion is decreased inevitably. Thus, there is a disadvantage in that it is not possible to obtain polybenzimidazole having a high molecular weight.

REFERENCES

[Non-patent Documents]

Non-patent Document 1: T. S. Chung, *Journal of Macromolecular Science, Part C* 37:2 (1997) 277-301

Non-patent Document 2: H. Vogel et al., *Journal of polymer Science*, 50 (1961) 511.

Non-patent Document 3: F. L. Hedberg et al., *Journal of Polymer Science*, 12 (1974) 1823-1828.

SUMMARY

An embodiment of the present disclosure is directed to providing a pure isophthalaldehyde bisulfite adduct free from impurities, such as non-reacted materials or byproducts, and a novel method for preparing the same.

In one aspect, there is provided a pure isophthalaldehyde bisulfite adduct free from impurities, represented by the following Chemical Formula 1:

[Chemical Formula 1]

The pure isophthalaldehyde bisulfite adduct may be for use in polymerization of polybenzimidazole under a mild condition in an organic solvent.

In another aspect, there is provided a method for preparing a pure isophthalaldehyde bisulfite adduct free from impurities, the method including: I) dissolving sodium bisulfite into distilled water and dissolving isophthalaldehyde into methanol, mixing the two solutions to carry out a reaction at 10-30° C., and filtering and drying the reaction mixture to obtain an isophthalaldehyde bisulfite adduct; II) dissolving the resultant adduct into water with sodium bisulfite to further carry out a reaction and adding methanol thereto to precipitate the adduct, followed by filtering and drying to carry out preliminary purification; and III) dissolving the preliminarily purified adduct into an organic solvent, filtering the non-dissolved excessive starting materials and inorganic salt, further precipitating the filtrate, and further filtering and drying the precipitate to carry out secondary purification.

In step I), sodium bisulfite may be used in a ratio of 2-3 equivalents to 1 equivalent of isophthalaldehyde.

In step III), the organic solvent may be any one selected from the group consisting of dimethyl sulfoxide (DMSO), dimethyl acetamide (DMAc), dimethylformamide (DMF), N-methylpyrrolidone (NMP) and a mixture thereof.

In step III), the filtrate may be further precipitated with acetone, isopropyl alcohol or hexane.

According to the present disclosure, it is possible to obtain a pure isophthalaldehyde bisulfite adduct free from impurities, such as unreacted materials or byproducts. In addition, it is possible to accomplish industrial mass production of a high-molecular weight polybenzimidazole by using the adduct as a starting material for polymerizing polybenzimidazole under a mild condition in an organic solvent.

DETAILED DESCRIPTION OF EMBODIMENTS

The pure isophthalaldehyde bisulfite adduct and the novel method for preparing the same of the present disclosure will become apparent from the following description of the embodiments with reference to the accompanying drawings, which is set forth hereinafter.

In one aspect, there is provided a pure isophthalaldehyde bisulfite adduct free from impurities, represented by the following Chemical Formula 1:

[Chemical Formula 1]

According to the related art, when using isophthalic acid as one of the monomers for preparing polybenzimidazole, a neutralization process is required. In another case, when using an isophthalaldehyde bisulfite adduct as a monomer, there is a disadvantage in that it is difficult to polymerize high-molecular weight polybenzimidazole since the isophthalaldehyde bisulfite adduct still contains impurities, such as unreacted material or byproducts.

However, unlike the conventional process for polymerizing polybenzimidazole using a strongly acidic polymerization solvent, the pure isophthalaldehyde bisulfite adduct free from impurities according to the present disclosure is used as a monomer for polymerizing polybenzimidazole under a mild condition in an organic solvent, such as dimethyl acetamide, and thus allows industrial mass production of high-molecular weight polybenzimidazole.

The pure isophthalaldehyde bisulfite adduct free from impurities, represented by the above Chemical Formula 1 is obtained fundamentally as depicted by the following Reaction Scheme. Particularly, isophthalaldehyde reacts with sodium bisulfite to produce an isophthalaldehyde bisulfite adduct, wherein the oxygen anion of sodium bisulfite functions as a nucleophile to be bound to the ketone structure of isophthalaldehyde to perform a reaction.

[Reaction Scheme]

In other words, the present disclosure provides a method for preparing a pure isophthalaldehyde bisulfite adduct free from impurities, the method including: I) dissolving sodium bisulfite into distilled water and dissolving isophthalaldehyde into methanol, mixing the two solutions to carry out a reaction at 10-30° C., and filtering and drying the reaction mixture to obtain an isophthalaldehyde bisulfite adduct; II) dissolving the resultant adduct into water with sodium bisulfite to further carry out a reaction and adding methanol thereto to precipitate the adduct, followed by filtering and drying to carry out preliminary purification; and III) dissolving the preliminarily purified adduct into an organic solvent, filtering the non-dissolved excessive starting materials and inorganic salt, further precipitating the filtrate, and further filtering and drying the precipitate to carry out secondary purification.

First, in step I), isophthalaldehyde is allowed to react with sodium bisulfite to obtain an isophthalaldehyde bisulfite adduct. Herein, sodium bisulfite may be used in a ratio of 2-3 equivalents to 1 equivalent of isophthalaldehyde. This is because sodium bisulfite itself has slightly insufficient nucleophilic property to complete the reaction and sodium bisulfite frequently exists as a dimeric form, resulting in a deficiency in terms of equivalents required for the reaction.

Sodium bisulfite is dissolved in distilled water and isophthalaldehyde is dissolved in methanol, and then the two solutions are mixed and reacted at 10-30° C. under thorough agitation. In a temperature range of 10-30° C., there is no difference in reactivity. Then, the white milky precipitated product produced from the reaction of the reactants is filtered through a Buchner funnel by using a vacuum pump, and filtered in an oven under vacuum. In this manner, it is possible to obtain an isophthalaldehyde bisulfite adduct. The isophthalaldehyde bisulfite adduct obtained from step I) has low purity, since it still contains unreacted materials.

Next, in step II), the low-purity isophthalaldehyde bisulfite adduct containing unreacted materials, obtained from step I), is allowed to react further by dissolving the adduct in water with sodium bisulfite. Then, methanol is added thereto to precipitate the adduct, followed by filtering and drying. In this manner, the adduct is purified preliminarily.

Finally, the preliminarily purified adduct is dissolved in an organic solvent, and the non-dissolved excessive starting materials and inorganic salt are filtered. Then, the filtrate is further precipitated and the precipitate is further filtered and dried to carry out secondary purification. In this manner, it is possible to obtain the target product, i.e., pure isophthalaldehyde bisulfite adduct. Herein, the preliminarily purified adduct is dissolved in any one organic solvent selected from the group consisting of dimethyl sulfoxide (DMSO), dimethyl acetamide (DMAc), dimethyl formamide (DMF), N-methyl pyrrolidone (NMP) and a mixture thereof in order to remove the excessively introduced sodium bisulfite and inorganic salt formed as a byproduct. In this case, the final product is dissolved rapidly, while the excessively introduced residual sodium bisulfite and inorganic salt remain undissolved. In addition, the resultant solution is passed through a syringe filter to remove the undissolved sodium bisulfite to provide a filtrate in the state of a colorless transparent liquid having no floating materials. Then, the filtrate is further precipitated in acetone isopropyl alcohol or hexane, and the precipitate is further filtered through a fine filter paper and dried in a vacuum oven. In this manner, it is possible to obtain a pure isophthalaldehyde bisulfite adduct.

The examples and experiments will now be described. The following examples and experiments are for illustrative purposes only and not intended to limit the scope of this disclosure.

[Example] Preparation of Pure Isophthalaldehyde Bisulfite Adduct

I) Preparation of Isophthalaldehyde Bisulfite Adduct Containing Unreacted Materials First, each of 500 mL of methanol and 75 mL of distilled water is introduced to a beaker having an adequate size. Next, 5 g of isophthalaldehyde is dissolved into methanol and 23.145 g of sodium bisulfite is dissolved into distilled water. After checking both starting materials are dissolved completely, the sodium bisulfite solution is poured first into a 1000 mL round flask and then the isophthalaldehyde solution is poured thereto. The reaction materials are allowed to react by using a magnetic bar at room temperature for 24 hours. It can be observed that the solution becomes less transparent with the lapse of time, while a white precipitate is formed. After the completion of the reaction, the precipitate is filtered by using a Buchner funnel and a vacuum pump, dried in a vacuum oven at 80° C. for 2 days, and pulverized with a mortar to obtain an isophthalaldehyde bisulfite adduct containing unreacted materials.

II) Preliminary Purification

Then, 75 mL of distilled water is introduced to a beaker having an adequate size. The isophthalaldehyde bisulfite adduct containing unreacted materials, obtained from step I), and 23.145 g of sodium bisulfite are dissolved in turn thereto. After the reaction materials are dissolved completely until the solution becomes transparent, the solution is poured into 500 mL of methanol. It can be observed that a white precipitate is formed. After agitating the solution for 30 minutes or less, the precipitate is filtered by using a Buchner funnel and a vacuum pump, dried in an oven under vacuum at 80° C., and then pulverized finely with a mortar to carry out preliminary purification.

III) Secondary Purification

Then, 5 g of the preliminarily purified isophthalaldehyde bisulfite adduct obtained from step II) is dissolved in 50 mL of dimethyl sulfoxide as a solvent. A small amount of undissolved floating materials is observed. After that, the floating materials are filtered by using a syringe filter and the remaining solution is precipitated in 200 mL of acetone. When a white precipitate is observed, it is collected in portions and separated out by using a centrifugal separator. Finally, the resultant product is dried in an oven under vacuum at 80° C. to obtain a pure isophthalaldehyde bisulfite adduct free from unreacted materials and byproducts.

[Comparative Example] Preparation of Isophthalaldehyde Bisulfite Adduct Containing Unreacted Materials An isophthalaldehyde bisulfite adduct containing unreacted materials is obtained by the same method as Example, except that the preliminary purification of II) is not performed.

Figure 1:
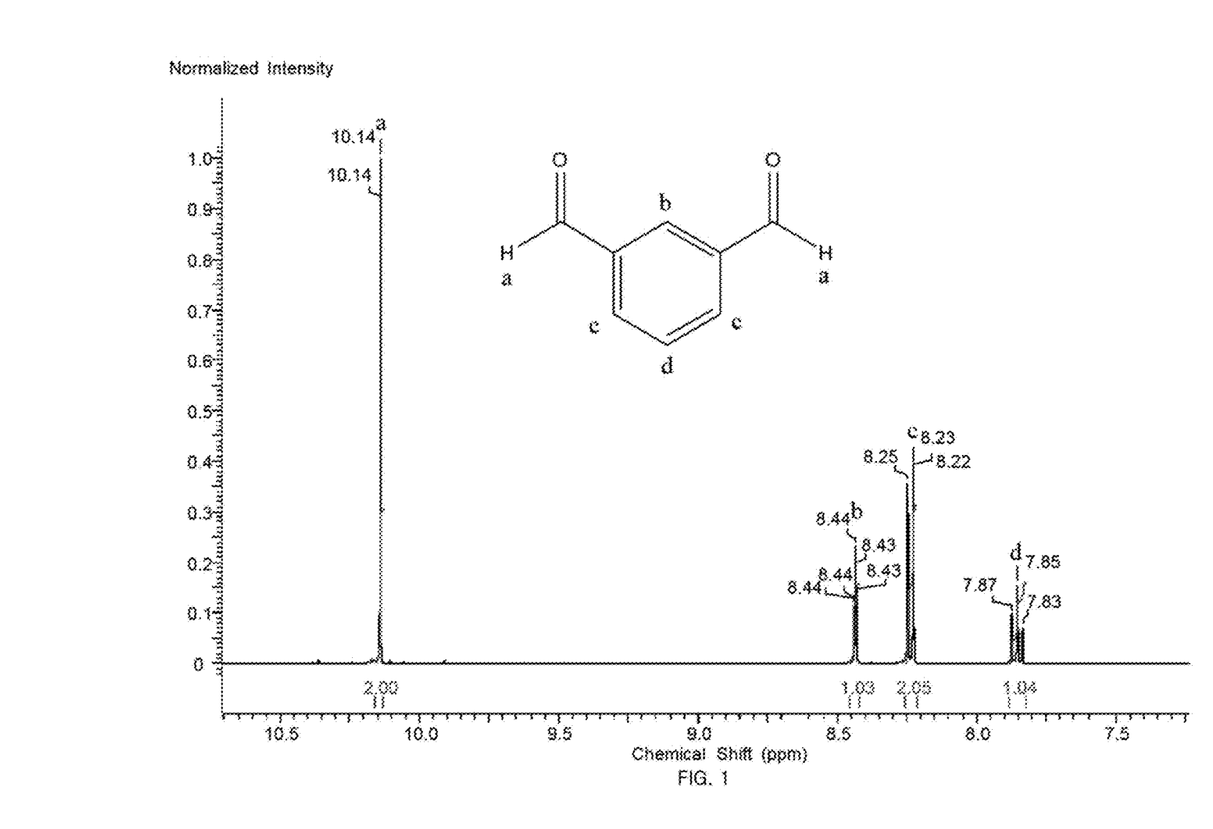
FIG. 1 shows the $^1$H-NMR spectrum of isophthalaldehyde that is a reactant used for preparing the isophthalaldehyde bisulfite adduct according to an embodiment.

FIG. 1 shows the $^1$H-NMR spectrum of isophthalaldehyde that is a reactant used for preparing the isophthalaldehyde bisulfite adduct according to an embodiment. As shown in FIG. 1, it can be seen that the peak at δ 10.14 results from the hydrogen atoms of aldehyde groups in the structure. [δ (ppm)=7.83-8.44 (4H, aromatic), 10.14 (2H, C—H of aldehyde groups)].

Figure 2A:
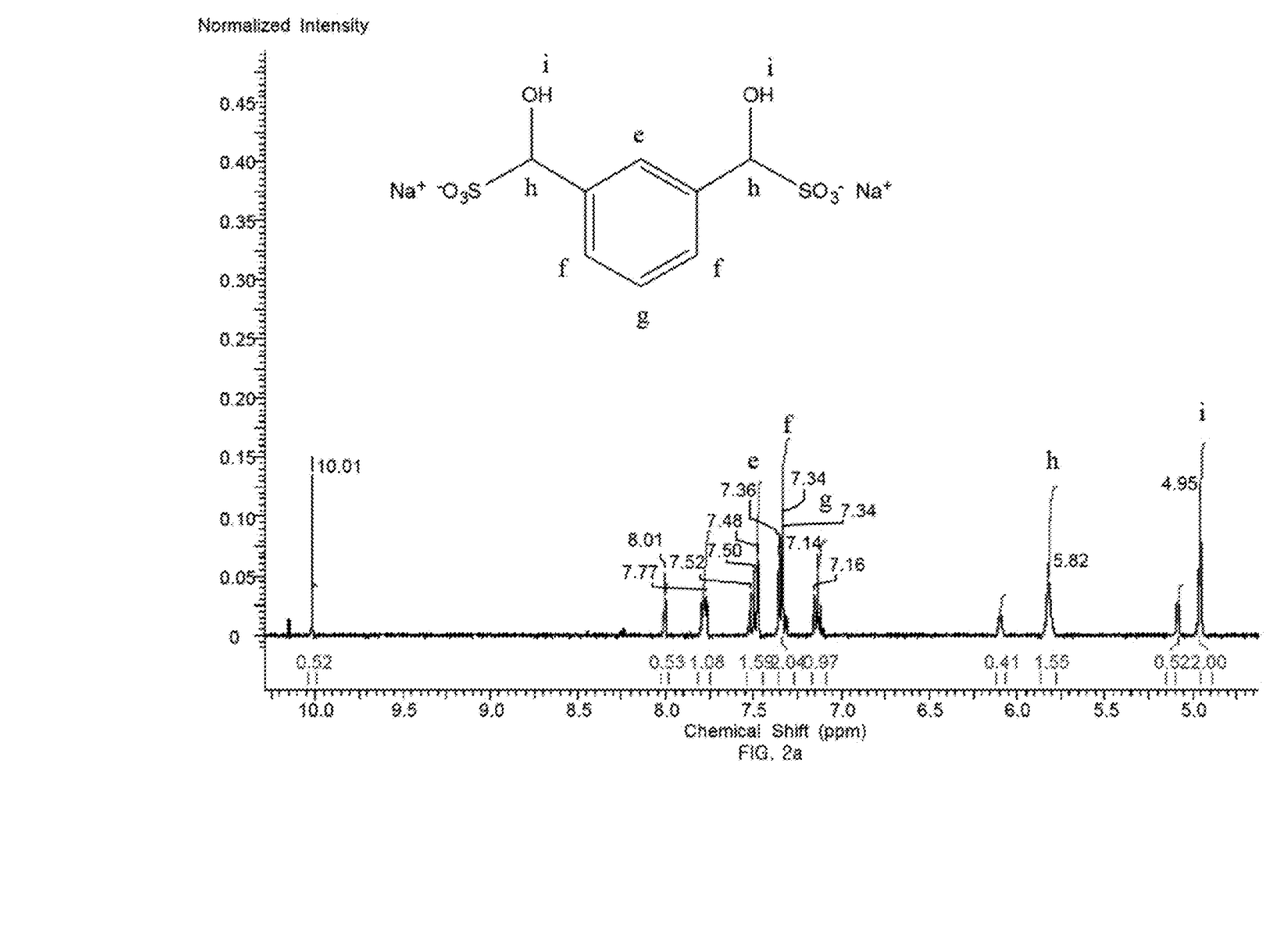
FIG. 2A shows the $^1$H-NMR spectrum of an unreacted material-containing isophthalaldehyde bisulfite adduct obtained from Comparative Example.
Figure 2B:
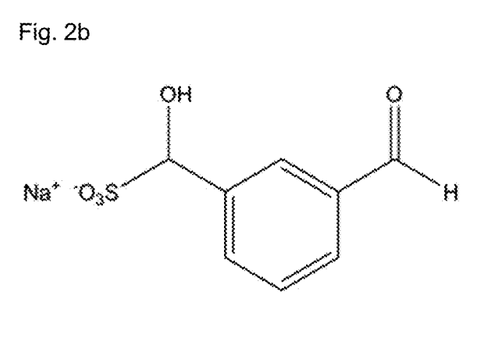
FIG. 2B shows the structural formula of an incomplete adduct compound related with the peaks of unreacted materials.

In addition, FIG. 2 shows the $^1$H-NMR spectrum (portion (A)) of an unreacted material-containing isophthalaldehyde bisulfite adduct obtained from Comparative Example, and the structural formula (portion (B)) of an incomplete adduct compound related with the peaks of unreacted materials. As shown in portion (A) of FIG. 2, it can be seen that an isophthalaldehyde bisulfite adduct is obtained by identifying the peaks at δ 4.95 resulting from the O—H hydrogen atoms in the hydroxyl groups, at δ 5.82 resulting from sp$_3$ C—H hydrogen atoms and at δ 7.14-7.52 resulting from the aromatic hydrogen atoms of benzene rings. Further, the remaining peaks, such as those at δ 10.01, result from the unreacted material, aldehyde, as shown in FIG. 1, or the semi-finished product such as the structural formula of the incomplete adduct compound as shown in portion (B) of FIG. 2.

Figure 3A:
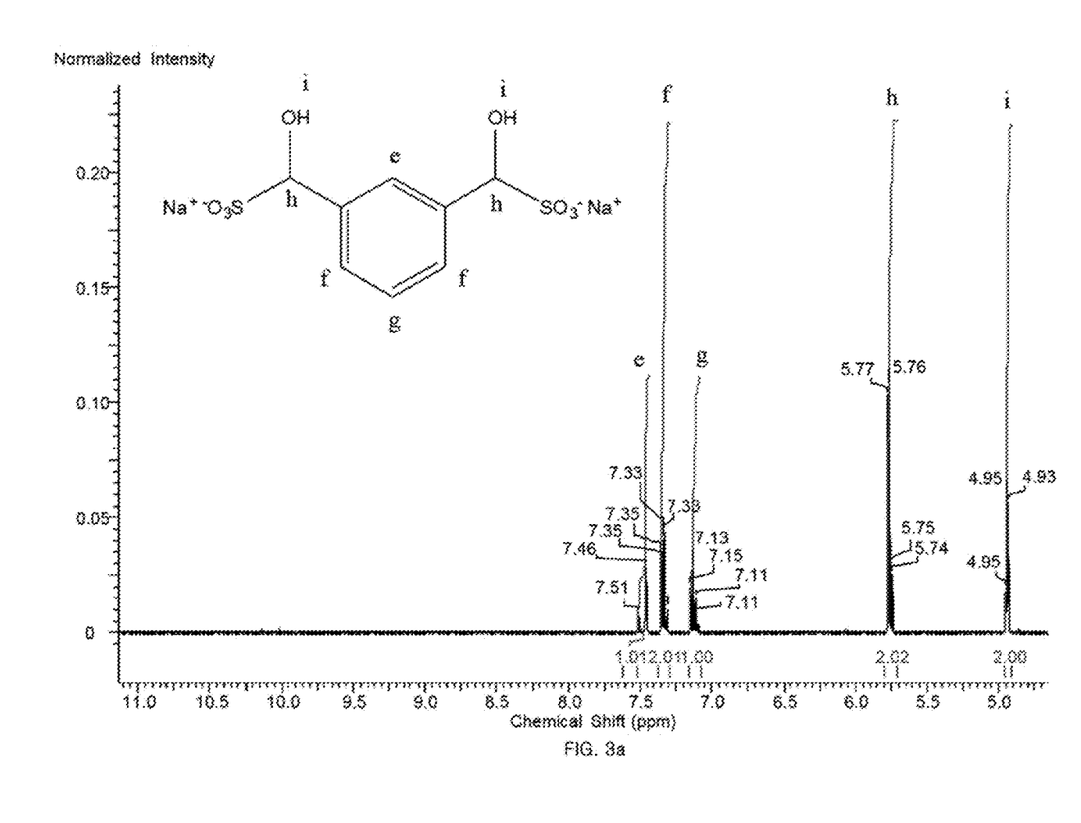
FIG. 3A shows the $^1$H-NMR spectrum of a pure isophthalaldehyde bisulfite adduct free from unreacted materials according to an embodiment.
Figure 3B:
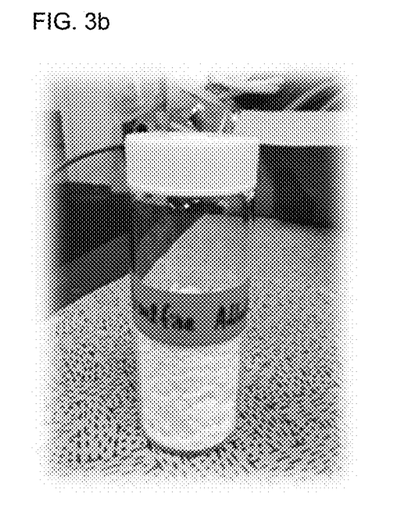
FIG. 3B shows the actual photographic image of the resultant sample.

Meanwhile, FIG. 3 shows the $^1$H-NMR spectrum (portion (A)) of a pure isophthalaldehyde bisulfite adduct free from unreacted materials according to an embodiment, and the actual photographic image (portion (B)) of the resultant sample. As compared to the spectrum of portion (A) of FIG. 2, it can be seen that the peaks of unreacted materials, such as those at δ 10.01, disappear completely. This demonstrates that a pure isophthalaldehyde bisulfite adduct having a purity of 100% and free from impurities, such as unreacted materials and byproducts, is obtained according to an embodiment of the present disclosure. [δ (ppm)=4.93-4.95 (2H, O—H), 5.74-5.77 (2H, sp$_3$ C—H), 7.11-7.51 (4H, aromatic)].

What is claimed is:

1. A method for preparing a pure isophthalaldehyde bisulfite adduct free from impurities, the method comprising:
   I) dissolving sodium bisulfite into distilled water and dissolving isophthalaldehyde into methanol, mixing the two solutions to carry out a reaction at 10-30° C., and filtering and drying the reaction mixture to obtain an isophthalaldehyde bisulfite adduct;
   II) dissolving the resultant adduct into water with sodium bisulfite to further carry out a reaction and adding methanol thereto to precipitate the adduct, followed by filtering and drying to carry out preliminary purification; and
   III) dissolving the preliminarily purified adduct into an organic solvent, filtering the non-dissolved unreacted starting materials and an inorganic salt, further precipitating the filtrate, and further filtering and drying the precipitate to carry out secondary purification.

2. The method for preparing a pure isophthalaldehyde bisulfite adduct free from impurities according to claim 1, wherein sodium bisulfite is used in a ratio of 2-3 equivalents to 1 equivalent of isophthalaldehyde, in step I).

3. The method for preparing a pure isophthalaldehyde bisulfite adduct free from impurities according to claim 1, wherein the organic solvent is any one selected from the group consisting of dimethyl sulfoxide (DMSO), dimethyl acetamide (DMAc), dimethylformamide (DMF), N-methyl-pyrrolidone (NMP) and a mixture thereof, in step III).

4. The method for preparing a pure isophthalaldehyde bisulfite adduct free from impurities according to claim 1, wherein the filtrate is further precipitated with acetone, isopropyl alcohol or hexane, in step III).

* * * * *